United States Patent
Iwataki et al.

(10) Patent No.: US 6,617,341 B1
(45) Date of Patent: Sep. 9, 2003

(54) INSECTICIDAL 2-IMINOTHIAZOLE DERIVATIVES

(75) Inventors: Isao Iwataki, Gainesville, FL (US); Asiye Meric, Eskisehir (TR); Elizabeth Laura Moyano, Cordoba (AR); Renpei Hatano, Kanagawa (JP)

(73) Assignee: Nippon Soda Co. Ltd., Tokyo (JP)

( * ) Notice: Subject to any disclaimer, the term of this patent is extended or adjusted under 35 U.S.C. 154(b) by 0 days.

(21) Appl. No.: 10/331,211

(22) Filed: Dec. 30, 2002

(51) Int. Cl.[7] .................. C07D 277/42; A01N 43/78
(52) U.S. Cl. ........................ 514/370; 548/197
(58) Field of Search ................... 548/197; 514/370

(56) References Cited

U.S. PATENT DOCUMENTS

| | | |
|---|---|---|
| 4,199,506 A | 4/1980 | Howe et al. |
| 4,284,426 A | 8/1981 | Howe et al. |
| 4,371,389 A | 2/1983 | Howe et al. |
| 4,437,875 A | 3/1984 | Howe et al. |
| 4,437,876 A | 3/1984 | Howe et al. |

FOREIGN PATENT DOCUMENTS

| | | |
|---|---|---|
| EP | 0566138 A1 | 10/1993 |
| GB | 2331748 | 2/1999 |
| JP | 6-25199 | 2/1994 |
| WO | WO 97/00862 * | 1/1997 |

* cited by examiner

*Primary Examiner*—Robert Gerstl
(74) *Attorney, Agent, or Firm*—Dennis G. LaPointe; Mason Law, P.A.

(57) ABSTRACT

A novel 2-iminothiazole derivatives and the use as an insecticide and acaricide of the compounds of formula (1):

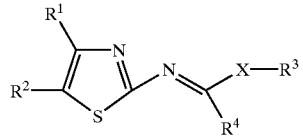

(1)

wherein $R^1$ is CN or fluoroalkyl (especially $C_1$–$C_4$ fluoroalkyl), $R^2$ is H, halogen or CN, $R^3$ is aryl, phenylalkyl, alkyl, cycloalkyl groups; being optionally substituted by one or more substituents, alkylthiocarbamoyl, or aroyl; being optionally substituted by one or more substituents, $R^4$ is aryl; being optionally substituted by one or more substituents, X is O, SOn, n is 0, 1 or 2 or X is $N(R^5)$ wherein, $R^3$ and $R^5$ are, independently, H or alkyl, alkoxy, acyl, alkylamino, aryl groups; being optionally substituted by one or more substituents or arylamino, being optionally substituted by one or more substituents or $R^3$ and $R^5$ may additionally be fused to a heteroaromatic ring.

5 Claims, No Drawings

INSECTICIDAL 2-IMINOTHIAZOLE DERIVATIVES

BACKGROUND OF THE INVENTION

1. Field of the Invention

The present invention relates to novel thiazole derivatives, which have insecticidal and acaricidal activity. The preparation and use, in agriculture and horticulture, of agrochemical compositions containing these novel insecticidal thiazoles are also disclosed.

2. Description of the Related Art

It is known in the art that certain thiazole derivatives such as those disclosed in U.S. Pat. Nos. 4,199,506, 4,284,426, 4,371,389, 4,437,875 and 4,437,876 have herbicide antidote properties and in Japan Kokai Koho 06-25199 have fungicidal properties. Furthermore, it is known in the art that UK patent application GB 2331748 discloses 5-cyano or thiocarbamoyl thiazole derivatives and their use as insecticides, acaricides or nematocides. The present invention concerns the novel thiazole derivatives which have excellent insecticidal and acaricidal activity.

SUMMARY OF THE INVENTION

In accordance with the present invention, thiazole derivatives are provided having the formula (1):

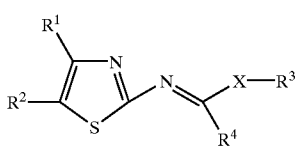

(1)

wherein $R^1$ is CN or fluoroalkyl, $R^2$ is H, halogen or CN, $R^3$ is aryl, phenylalkyl, alkyl, cycloalkyl groups ( being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), arylthiocarbonyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), aryl or alkylsulfonyl (being optionally substituted by one or more of halogen), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy).

X is O, $SO_n$, n is 0, 1 or 2.

or X is $N(R^5)$ wherein, $R^3$ and $R^5$ are, independently, H or alkyl, alkoxy, acyl, alkylamino, aryl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or $R^3$ and $R^5$ may additionally be fused to a heteroaromatic ring.

The present invention is directed to agrochemical compositions comprising as an active ingredient at least one of the novel thiazole derivatives of the present invention, as well as to the use of these active ingredients or compositions for pest control, and, in particular as insecticides and acaricides useful in agriculture and horticulture.

For a better understanding of the present invention, reference is made to the following description and its scope will be pointed out in the appended claims.

DETAILED DESCRIPTION OF THE INVENTION

For purposes of the present invention the general terms used hereinabove and hereinbelow have the following meanings, unless otherwise defined:

Alkyl groups are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl, or 3-hexyl.

Cycloalkyl groups are generally cyclopropyl, cyclobutyl, cyclopentyl, cyclohexyl.

Halogen and halo substituents will be understood generally as meaning fluoro, chloro, bromo, iodo. chloro, bromo, or iodo are preferred meanings in this invention.

Haloalkyl can contain identical or different halogenatoms, typically fluoromethyl, difluoromethyl, difluorochloromethyl, trifluoromethyl, chloromethyl, trichloromethyl Fluoroalkyl is generally fluoromethyl, difluoromethyl, trifluoromethyl, pentafluoroethyl, n-heptafluoroprpyl, n-nonafluorobutyl, n-undecafluoropentyl, n-tridecafluorohexyl and preferably trifluoromethyl and pentafluoroethyl.

Alkoxy is typically methoxy, ethoxy, propyloxy, isopropyloxy, n-butyloxy, isobutyloxy, sec-butyloxy, and tert-butyloxy, methoxy and ethoxy are preferred.

Aryl is typically substituted phenyl or naphthyl, furyl, thienyl, six-membered heteroaromatic ring system such as pyridinyl, pyrimidinyl, pyridazinyl, pyrazinyl, triazinyl (1,2, 3-, 1,2,4- and 1,3,5-), quinolinyl, isoquinolinyl, cinnolinyl, quinazolinyl, quinoxalinyl, indolinyl, isoindolinyl, five membered heteroaromatic ring such as thiazolyl, isothiazolyl, oxazolyl, isoxazolyl, pyrazolyl, thiadiazolyl oxadiazolyl, pyrollyl, imidazolyl, triazolyl (1,2,3- and 1,2, 4-), tetrazolyl, fused five membered rings such as benzofuranyl, benzothienyl, benzimidazolinyl; being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy.

Aroyl is typically substituted benzoyl; being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy.

Alkenyl and alkynyl groups preferably contain from 2 to 6, more preferably from 2 to 4, carbon atoms. They can be in the form of straight or branched chains, and, where appropriate, the alkenyl groups can be of either (E)- or (Z)-configuration. Examples are vinyl, allyl, propargyl.

The alkylenedioxy groups are optionally substituted with halogene (especially fluorine) and are such as methylenedioxy or difluoromethylenedioxy.

The present invention provides the use as insecticides or acaricides of thiazole derivatives having the following formula (1):

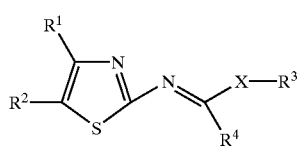

(1)

wherein $R^1$ is CN or fluoroalkyl (especially $C_1$–$C_4$ fluoroalkyl), $R^2$ is H, halogen or CN, $R^3$ is aryl, phenylalkyl, alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy).

X is O, $SO_n$, n is 0, 1 or 2.

or X is $N(R^5)$ wherein, $R^3$ and $R^5$ are, independently, H or alkyl, alkoxy, acyl, alkylamino, aryl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or $R^3$ and $R^5$ may additionally be fused to a heteroaromatic ring.

Examples of specific compounds of formula (1), which are of use as insecticides and acaricides include the compounds listed in Table I at end of this disclosure. NMR data of oily substances in the formula 1 are shown in Table 2, which also follows at the end of this disclosure.

The present invention also provides a process for the preparation of a compound of (1) as defined above which comprises (a) reacting a compound of the general formula

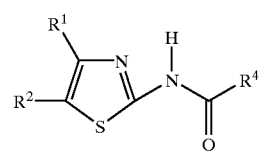

(2)

in which $R^1$, $R^2$ and $R^4$ are as defined above with phosphorous pentachloride and phosphorous oxychloride to produce the intermediate (3)

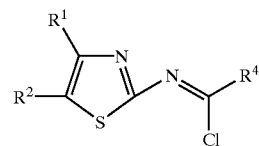

(3)

(b) reacting a compound of the general formula (3) in which $R^1$, $R^2$ and $R^4$ are as defined above with $R^3$—X—A in which X is O or S, $R^3$ is defined above and A is an alkali metal radical such as Na or K, or $R^3$—X—H in which X is N—$R^5$ with an inorganic base such as NaH, NaOH, KOH, $K_2CO_3$, $Na_2CO_3$ or an organic amine such as pyridine, triethylamine, imidazole to produce (1).

(c) reacting a compound of the general formula (3) in which $R^1$, $R^2$ and $R^4$ are as defined above with thiourea to produce the intermediate (4) followed by reacting an alkali metal salt of the general formula (4) with $R^3$—Y in which $R^3$ is alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl

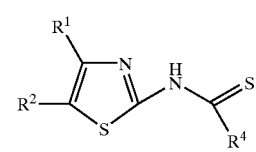

(4)

(being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy) and Y is halogen to produce (1) in which $R^1$, $R^2$ and $R^4$ are defined above and X is S and $R^3$ is as defined above.

The procedure of step (a) is carried out in the excess amount of phosphorous oxychloride without other solvents at the reflux temperature. The procedure of step (b) is conveniently carried out in the presence of a solvent. Suitable solvents include aprotic solvents such as benzene, acetone, methylethyl ketone, chloroform, acetonitrile, tetrahydrofuran, dioxane, DMSO, DMF at a temperature in the range from 0° C. to a reflux temperature of the solvent. The procedure of step (c), formation of the compound of the general formula (4) is carried out in methanol, ethanol, tetrahydrofuran, dioxane, DMSO, DMF at a temperature range from 50° C. to a reflux temperature of the solvent. The next procedure to the formation of a compound of the general formula (1) is carried out in tetrahydrofuran, dioxane, DMSO, DMF at a temperature range from 0° C. to a reflux temperature of the solvent. Surprisingly, it has now been found that the novel compounds of formula (1) have, for practical purposes, a very advantageous spectrum of activities for protecting plants against insect and acarine pests, include such as Coleoptera, Diabrotica, Diptera, Homoptera and Lepidoptera, Heteroptera, Thysanoptera, Orthoptera and Acarina. The pests include those pests associated with agriculture, horticulture and animal husbandry, forestry, the storage of products of vegetable origin, such as fruit, grain, and timber, and also those pests associated with the transmission of diseases of man and animals.

Examples of insect and acarine pest species which may be controlled by the compounds of formula (1) include: *Pieris brassicae* (white butterfly), *Pseudaletia separata* (rice armyworm), *Heliothis virescens* (tobacco budworm), Trialeurodes spp. (white flies), *Aedes aegypti* (mosquito), Agrotis spp. (cutworms), *Blatta orientalis* (cockroach), Anopheles spp. (mosquitos), *Chilo partellus* (maize stem borer), Culex spp. ((mosquitos), *Dysdercus fasciatus* (capsid), *Musca domestica* (housefly), *Plutella xylostella* (diamond back moth), Aonidiella spp. (scale insects), *Bemisia tabaci* (sweetpotato white fly), *Blattella germanica* (German cockroach), *Myzus persicae* (green peach aphid), *Aphis gossypii* (cotton aphid), *Aphis fabae* (bean aphid), *Periplaneta americana* (American cockroach), *Phaedon cochleariae* (mustard beetle), *Spodoptera littoralis* (cotton leafworm), *Chortiocetes terminifera* (locust), Diabrotica spp. (rootworms), *Nilaparvata lugens* (brown rice planthopper), *Nephotettix cincticeps* (green rice leafhopper), *Tetranychus cinnabarinus* (carmine spider mite), *Panonychus ulmi* (European red mite), *Phyllocoptruta oleivora* (citrus rust mite), *Panonychus citri* (citrus red mite), *Tetranychus urticae* (two-spotted spider mite), *Polyphagotarsonemus latus* (brode mite) and Brevipalpus spp. (mites).

Compounds of the formula (1) are normally used in the form of compositions and can be applied to the crop or plant to be treated, simultaneously with or in succession with other compounds such as fertilizers, micronutrient donors or other preparations which influence the growth of plants. The thiazole derivatives of formula (1) can also be selectively combined with herbicides, as well as, other insecticides, fungicides, bactericides, nematocides, molluscicides or mixtures of several of these preparations and, if desired together with further carriers, surfactants or application promoting adjuvants employed in the art of formulation. In some cases, by mixing of the thiazole derivatives of formula (1) with other insecticides, results in synergistic insecticidal activity.

When applying the compound of the present invention in a practical way, the compound may be applied in a form as it is without adding other components. When the compound of the present invention is applied for plant protection purpose, the compound can be prepared into general types of formulations for plant protection use, such as wettable powder, granules, dust, emulsifiable concentrate, water soluble powder, suspension concentrate, flowable liquid, and so on.

In case the compound of the present invention is prepared into a solid type formulation, appropriate additives and carriers may be incorporated with the compound. Examples of the additive and the carrier include phytogenic powders, such as soybean powder and flour, mineral fine powders, such as diatomaceous earth, apatite, gypsum, talc, bentonite, pyrophyllite and clay, and organic and inorganic compounds, such as sodium benzoate, urea and Glauber's salt. In case the compound of the present invention is prepared into a liquid type formulation, an appropriate solvent is used for dissolving or dispersing the compound in the liquid type formulation. Examples of the solvent used for the liquid formulation include petroleum fractions, such as kerosene, xylene and solvent naphtha, cyclohexane, cyclohexanone, dimethylformamide, dimethylsulfoxide, alcohol, acetone, methyl isobutyl ketone, mineral oils, vegetable oils and water.

In addition, in order to provide uniformity and stability to the compound in the prepared formulations, it is possible to add surface active agents into each formulation upon necessity. There is no limitation for the surface active agent, and examples of the surface active agent that can be added to the above-mentioned formulations include nonionic surface active agents, such as polyoxyethylene-added alkyl ether, polyoxyethylene-added higher fatty acid ester, polyoxyethylene-added sorbitan higher fatty acid ester and polyoxyethylene-added tristyryl phenyl ether, a sulfate ester of polyoxyethylene-added alkyl phenyl ether, an alkyl benzene sulfonate, a polycarbonate, a lignin sulfonate, a formaldehyde condensate of alkyl naphthalene sulfonate, and a copolymer of isobutylene and maleic anhydride.

In general, the content of an active ingredient in each of the formulations recited above is preferably in a range of from 0.01 to 90% by weight, and more preferably from 0.05 to 85% by weight based on the total weight of the formulation. Each of the prepared formulations, such as wettable powder, emulsifiable concentrate, suspension concentrate and flowable solution, is diluted with water to be prepared and adjusted into the suspension or emulsion with a desired concentration, and is applied to crop plants. For the formulations, such as granular and dust formulations, the formulation itself is directly applied to the target crop plants or soil.

Needless to say that the compound alone according to the present invention has sufficient insecticidal and acaricidal activity, however, it can be combined for the use with one or more of various types of other plant protection chemicals, for example, fungicides, insecticides, acaricides and synergists.

Hereunder, representative examples for fungicides, insecticides, acaricides and plant growth regulators those which can be combined to use with the compound according to the present invention will be recited below.
Fungicides:
Captan, Folpet, Thiuram, Ziram, Zineb, Maneb, Mancozeb, Propineb, Polycarbamate, Chlorothalonil, Quintozene, Captafol, Iprodione, Procymidone, Vinclozolin, Fluorimide, Cymoxanil, Mepronil, Flutolanil, Pencycuron, Oxycarboxine, Fosetyl aluminium, Propamocarb, Triadimefon, Triadimenol, Propiconazole, Diclobutrazol, Bitertanol, Hexaconazol, Microbutanil, Flusilazole, Etaconazole, Fluotrimazole, Flutriafen, Penconazole, Diniconazole, Cyproconazole, Fenarimol, Triflumizole, Prochloraz, Imazalyl, Pefurazoate, Tridemorph, Fenpropimorph, Triforine, Buthiobate, Pyrifenox, Anilazine, Polyoxins, Metalaxyl, Oxadixyl, Furalaxyl, Isoprothiolane, Probenazole, Pyrrolenitrine, Blastocidin-S, Kasugamycin, Balidamycin, Dihydrostreptomycin sulfate, Benomyl, Carbendazim, Thiophanate methyl, Hymexazol, Basic copper chloride, Basic copper sulfate, Fentin acetate, Triphenyltin hydroxide, Diethofencarb, Metasulfocarb, Quinomethionate, Binapacryl, Lecithin, Sodium hydrogencarbonate, Dithianone, Dinocap, Fenaminosulf, Diclomezine, GuazatineDodine, IBP, Edifenphos, Mepanipyrim, Ferimzone, Trichlamide, Metasulfocarb, Fluazinam, Ethoquinolac, Dimetomorph, Pyroquilon, Tecloftalam, Fthalide, Fenazine oxide, Thiabedazole, Tricyclazole, Vinclozolin, Cymoxanil, Cyclobutanil, Guaztine, Propamocarb hydrochloride, Oxolinic acid.

Insecticides and Acaricides:

Organophosphorous and carbamate insecticides: Fenthion, Fenitrothion, Diazinon, Chlorpyrifos, ESP, Vamidothion, Fenthoate, Dimethoate, Formothion, Malathion, Trichlorfon, Thiometon, Phosmet, Dichlorvos, Acephate, EPBP, Methyl parathion, Oxadimeton methyl, Ethion, Salithion, Cyanophos, Isoxathione, Pyridafenthion, Phosalone, Methidathion, Sulprofos, Chlorfevinphos, Tetrachlorvinphos, Dimethylvinphos, Propaphos, Isofenphos, Ethyl thiometon, Profenophos, Pyraclofos, Monocrotophos, Azinphos methyl, Aldicarb, Methomyl, Dithiocarb, Carbofuran, Carbosulfan, Benfuracarb, Furathiocarb, Propoxur, BPMC, MTMC, MIPC, carbaryl, Pyrimicarb, Ethiofencarb, Fenoxycarb, cartap, thiocyclam, bensultap, etc.

Pyrethroid insecticides: Permethrin, Cypermethrin, Deltamethrin, Fenvalerate, Fenpropathrin, Pyrethrin, Allethrin, Tetramethrin, Resmethrin, Dimethrin, Propathrin, Fenothrin, Prothrin, Fluvalinate, Cyfluthrin, Cyhalothrin, Flucythrinate, Ethofenprox, Cycloprothrin, Tralomethrin, Silafluofen, Brofenprox, Acrinathrin, etc.

Bezoyl urea and other insecticides: Diflubenzuron, Chlorfluazuron, Hexaflumuron, Triflumuron, Tetrabenzuron, Fulfenoxuron, Flucycloxuron, Buprofezin, Pyriproxyfen, Methoprene, Benzoepin, Diafenthiuron, Imidacloprid, Fipronyl, Nicotin sulfate, Rotenone, Metaldehyde, Machine oil, Microbial insecticides such as BT and insect-pathogenic viruses, etc.

NEMATICIDES: Fenamiphos, Fosthiazate, etc.

Acaricides:

Chlorbenzilate, Fenisobromolate, Dicofol, Amitraz, BPPS, Benzomate, Hexythiazox, Fenbutatin oxide, Polynactin, Quinomethionate, CPCBS, Tetradifon, Avermectin, Milbemectin, Clofentezin, Cyhexatin, Pyridaben, Fenpyroxymate, Tebufenpyrad, Pyrimidifen, Fenothiocarb, Dienochlor, etc.

Plant Groth Regulators: Gibberellins(e.g., Gibberellin A3, Gibberellin A4, Gibberellin A7), IAA, NAA, etc.

EXAMPLES

The following examples serve to provide further appreciation of the invention but are not meant in any way to restrict the effective scope of the invention. The structures of isolated novel compounds were confirmed by NMR, Mass, or other appropriate analysis.

Example 1

N-(5-Iodo-4-trifluoromethylthiazol-2-yl)-3-trifluoromethylbenzimidoyl Chloride

N-(5-Iodo-4-trifluoromethylthiazol-2-yl)-3-trifluoromethylbenzamide (9.3 g was mixed with phosphorous pentachloride (4.2 g) and phosphorous oxychloride (25 ml) and the mixture was refluxed for 7 hr. The excess phosphorous oxychloride was removed under reduced pressure and the residue was mixed with cold water then extracted with chloroform. The extract was dried over anhydrous magnesium sulfate and the solvent was removed under reduced pressure then the residue was recrystallized from chloroform-n-hexane to give N-(5-iodo-4-trifluoromethylthiazol-2-yl)-3-trifluoromethylbenzimidoyl chloride as yellow needles (8.5 g), m. p. 136–137° C.

Example 2

N-(5-Chloro-4-trifluoromethylthiazol-2-yl)-3-chlorobenzimidoyl Chloride

N-(5-Chloro-4-trifluoromethylthiazol-2-yl)-3-chlorobenzamide (15.5 g was mixed with phosphorous pentachloride (9.5 g) and phosphorous oxychloride (60 ml) and the mixture was refluxed for 12 hr. The excess phosphorous oxychloride was removed under reduced pressure and the residue was mixed with cold water then extracted with chloroform. The extract was dried over anhydrous magnesium sulfate and the solvent was removed under reduced pressure then the residue was recrystallized from n-hexane to give N-(5-chloro-4-trifluoromethylthiazol-2-yl)-3-chlorobenzimidoyl chloride; as pale brown needles (11.0 g), m. p. 89–90° C.

Example 3

N-(5-Iodo-4-trifluoromethyl)thiazol-2-yl-α-Propargyloxy-3-trifluoromethylbenzimide Propargyl alcohol (1 ml) and potassium t-butoxide (0.2 g) was mixed at room temperature with stirring then N-(5-iodo-4-trifluoromethylthiazol-2-yl)-3-trifluoromethylbenzimidoyl chloride (0.8 g) was added at the same temperature. The mixture was stirred for I hr at room temperature then it was mixed with water and extracted with chloroform. The chloroform layer was dried over anhydrous magnesium sulfate and the solvent was removed under reduced pressure. The residue was purified by silicagel column chromatography (n-hexane-chloroform 2:1 mixture as solvents) to give N-(5-Iodo-4-trifluoromethylthiazol-2-yl)-α-propargyloxy-3-trifluoromethylbenzimide (0.6 g) as white prisms, m. p. 77–78° C.

Example 4

N-(5-Iodo-4-trifluoromethylthiazol-2-yl)-3-trifluoromethylbenzimido Dimethyldithiocarbamate N-(5-Iodo-4-trifluoromethylthiazol-2-yl)-3-trifluoromethylbenzimidoyl chloride (1 g) was dissolved in tetrahydrofuran (10 ml) and DMSO (5 ml) and sodium dimethyldithiocarbamate 40% aqueous solution (0.9 g) was added at room temperature with stirring. The mixture was stirred for 2 hr at room temperature then poured into cold water and insoluble yellow solid was filtered. The solid was recrystallized from methanol to give N-(5-iodo-4-trifluoromethylthiazol-2-yl)-3-trifluoromethylbenzimido dimethyldithiocarbamate (0.6 g), as yellow prisms, m. p. 157–158° C.

Example 5

N-(5-Iodo-4-trifluoromethylthiazol-2-yl)-α-(imidazol-1-yl)-3-trifluoromethylbenzimide N-(5-Iodo-4-trifluoromethylthiazol-2-yl)-3-trifluoromethylbenzimidoyl chloride (0.8 g) was mixed with imidazole (I g) in tetrahydrofuran (10 ml). The mixture was refluxed for 2 hr with stirring then the solvent was removed under reduced pressure. The residue was mixed with and extracted with chloroform. The chloroform layer was dried over anhydrous magnesium sulfate and the solvent was removed under reduced pressure. The residue was recrystallized from carbon tetrachloride-methylene chloride to give N-(5-iodo-4-trifluoromethylthiazol-2-yl)-α-imidazol-1-yl-3-trifluoromethylbenzimide (0.5 g) as colorless crystals, m. p. 143–144° C.

Example 6

1-(5-Iodo-4-trifluoromethylthiazol-2-yl)-2-(3-trifluoromethylbenz)amidine

N-(5-Iodo-4-trifluoromethylthiazol-2-yl)-3-trifluoromethylbenzimidoyl chloride (2 g) was dissolved in tetrahydrofuran (10 ml) and 7N-ammonium hydroxide (5 ml) was added with stirring at room temperature. The mixture was stirred for 30 minutes at the same temperature then poured into ice water. The solid precipitated was filtered and dried. It was recrystallized from carbon tetrachloride-n-hexane to give 1-(5-Iodo-4-trifluoromethylthiazol-2-yl)-2-(3-trifluoromethylbenz) amidine as pale brown crystals (1.5 g), 107–108° C.

Example 7

N-(5-Chloro-4-trifluoromethylthiazol-2-yl)-α-(3,5-dimethylbenzoyl)oxy-(3-chlorobenz)imide Sodium methoxide (0.1 g) was dissolved in methanol (5 ml) and 3,5-dimethylbenzoic acid (0.3 g) was added then the solvent was removed under reduced pressure. The residue was mixed with tetrahydrofuran (10 ml) and N-(5-chloro-4-trifluoromethylthiazol-2-yl)-3-chlorobenzimidoyl chloride (0.7 g) was added with stirring. The mixture was refluxed for 4 hr then the solvent was removed under reduced pressure. The residue was mixed with water and extracted with chloroform. The extract was dried over anhydrous magnesium sulfate and the solvent was removed under reduced pressure. The residue was purified by silicagel column chromatography (n-hexane-chloroform 1:2 as solvents) to give N-(5-Chloro-4-trifluoromethylthiazol-2-yl)-α-(3,5-dimethylbenzoyl)oxy-(3-chlorobenz)imide (0.33 g which was recrystallized from carbon tetrachloride-n-hexane), m. p. 123–124° C.

Example 8

1-(5-Iodo-4-trifluoromethylthiazol-2-yl)-3-methoxy-2-(3-trifluoromethylbenz)amidine N-(5-Iodo-4-trifluoromethylthiazol-2-yl)-3-trifluoromethylbenzimidoyl chloride (1.2 g) was dissolved in pyridine (5 ml) and methoxyamine hydrochloride (0.8 g) was added at room temperature with stirring. The mixture was stirred for 1 hr at the same temperature and poured into cold water then acidified with diluted hydrochloric acid. The oily precipitates were extracted with chloroform. The chloroform layer was dried over anhydrous magnesium sulfate and the solvent was removed under reduced pressure. The residual solid was recrystallized from n-hexane to give 1-(5-iodo-4-trifluoromethylthiazol-2-yl)-3-methoxy-2-(3-trifluoromethylbenz)amidine (1.1 g) as yellow prisms, m. p. 107–108° C.

Example 9

3-Acetyl-1-(5-iodo-4-trifluoromethylthiazol-2-yl)-3-methoxy-2-(3-trifluoromethylbenz)amidine N-(5-Chloro-4-trifluoromethylthiazol-2-yl)-3-chlorobenzimidoyl chloride (0.8 g) and acetic anhydride (5 ml) was refluxed for 2 hr and the mixture was poured into ice water. The precipitate was extracted with chloroform. The extract was dried over anhydrous magnesium sulfate and the solvent was removed under reduced pressure. The residue was purified by silicagel column chromatography (chloroform-n-hexane 1:1 as solvents) to give 3-Acetyl-1-(5-iodo-4-trifluoromethylthiazol-2-yl)-3-methoxy-2-(3-trifluoromethylbenz)amidine (0.3 g, which was recrystallized from n-hexane as colorless prisms), m. p. 109–110° C.

Example 10

N-(5-Bromo-4-trifluoromethylthiazol-2-yl)-3-chloro-α-(4-toluoyl)thiobenzamidine

N-(5-bromo-4-trifluoromethylthiazol-2-yl)-3-chlorothiobenzamide (0.5 g) and sodium methoxide (0.07 g) was dissolved in methanol (10 ml) and the solvent was removed under reduced pressure. The residue was mixed in tetrahydrofurane (15 ml) and toluoyl chloride (0.2 g) was added at room temperature with stirring. The mixture was stirred for 2 hr at the same temperature and the mixture was poured into ice water then extracted with chloroform. The chloroform layer was dried over anhydrous magnesium sulfate and the solvent was removed under reduced pressure. The residue was purified by silicagel column chromatography (chloroform-n-hexane 1:1 as eluants) to give N-(5-bromo-4-trifluoromethylthiazol-2-yl)-3-chloro-α-(4-toluoyl)thiobenzamidine (0.078 g) as yellow oil. 1H-NMR (CDCl$_3$) δ 2.43 (s, 3H), 7.3 (m, 4H), 7.82 (d, 2H), 8.05 (d, 1H), 8.21 (s, 1H).

Examples for carrying out the formulations comprising the compound of the present invention will be explained. However, it should be noted that the type and incorporating rate of additives are not limited to those described in the following examples and may be modified over extensive range. Note that the term of "part" in the formulation example described below denotes "part by weight".

Example 11

Wettable Powder Formulation

| | |
|---|---|
| A compound of present invention | 40 part |
| Diatomaceous earth | 53 part |
| Higher alcohol sulfate | 4 part |
| Alkylnaphthalenesulfonate | 3 part |

The components given above are mixed and pulverized to fine particles to thereby give a wettable powder formulation for the compound of the present invention with the content of 40% based on the active ingredient.

Example 12

Emulsifiable Concentrate Formulation

| | |
|---|---|
| A compound of present invention | 30 part |
| Xylene | 33 part |
| Dimethylformamide | 30 part |
| Polyoxyethylene alkyl allyl ether | 7 part |

The components given above are mixed and prepared to a solution to thereby give an emulsifiable concentrate formulation for the compound of the present invention with the content of 30% based on the active ingredient.

Example 13

Dust Formulation

| A compound of present invention | 10 part |
|---|---|
| Talc | 89 part |
| Polyoxyethylene alkyl allyl ether | 1 part |

The components given above are mixed and pulverized to fine particles to thereby give a dust formulation for the compound of the present invention with the content of 10% based on the active ingredient.

Example 14

Granular Formulation

| A compound of present invention | 5 part |
|---|---|
| Clay | 73 part |
| Bentonite | 20 part |
| Dioctylsulfosuccinate sodium salt | 1 part |
| Sodium phosphate | 1 part |

The components given above are mixed, thoroughly grinded, added with water, then kneaded, and granulated, and further dried to thereby give a granular formulation for the compound of the present invention with the content of 5% based on the active ingredient.

Example 15

Suspension Concentrate Formulation

| A compound of present invention | 10 part |
|---|---|
| Sodium ligninsulfonate | 4 part |
| Sodium dodecylbenzenesulfonate | 1 part |
| Xanthane gum | 0.2 part |
| Water | 84.8 part |

The components given above are mixed and grinded by wet grinding to a particle size of less than 1 $\mu$m to thereby give a suspension concentrate for the compound of the present invention with the content of 10% based on the active ingredient.

Example 16

Efficacy against *Pseudaletia separata* Walker (*Ps*; Rice Armyworm)

A piece of Maize leaf (ca.7×1.5 cm) was dipped in the chemical solution at 125 ppm for 30 sec and air-dried. The leaf was placed in a glass petri dish (9 cm diameter) and five second-instar larvae of *Pseudaletia separata* were introduced into the petri dish. Five days after the treatment, the number of survival larvae was counted and the mortality was calculated by Abbott's formula.

Abbott's formula:

$$\text{mortality} = \frac{\text{Survival rate in untreated plot} - \text{Survival rate in treated plot}}{\text{Survival rate in untreated plot}} \times 100$$

Each test was duplicated. The results show that the following compounds had mortality of 100%: Compound Nos. 6,9,26,95,98,99,121 and 143.

TABLE 1

(1)

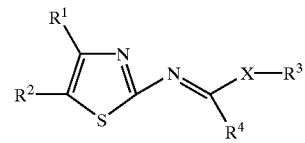

| Compound No. | R1 | R2 | R3 | R4 | X | m.p. |
|---|---|---|---|---|---|---|
| 1 | CF3 | Cl | Me | n-C6H13—C6H4 | O | |
| 2 | CF3 | Cl | Et | 1-naphthyl | S | |
| 3 | CF3 | Cl | 2,4-Cl2—C6H3CO | 4-C6H4—C6H4 | O | |
| 4 | CF3 | Cl | 4-F—C6H4 | 3-OCF3—C6H4 | O | |
| 5 | CF3 | I | propargyl | 3-CF3—C6H4 | O | 77–78 |
| 6 | CF3 | CN | H | 3-CF3—C6H4 | N—OMe | 170–171 |
| 7 | CF3 | CN | Me2NCS | 3-CF3—C6H4 | S | |
| 8 | CF3 | Br | 4-Me2N—C6H4CO | 3,5-Me2—C6H3 | O | |
| 9 | CF3 | I | 1-1,2,4-triazolyl | 3-CF3—C6H4 | | 147–148 |
| 10 | CF3 | Cl | 4-MeOCOCH2—C6H4CO | C6H5 | O | |
| 11 | CF3 | I | 1-imidazolyl | 4-t-Bu—C6H4 | | |
| 12 | CF3 | Br | CN | 3-CF3—C6H4 | NH | |
| 13 | CF3 | F | H | 4-Cl—C6H4 | NH | |
| 14 | CF3 | Br | 4-NO2—C6H4CO | 2,4-Cl2—C6H3 | S | |
| 15 | C3F7 | I | Me | 4-Cl—C6H4 | O | |
| 16 | CF3 | F | Ac | 2,4-Cl2—C6H3 | S | |
| 17 | CF3 | I | SO2CF3 | 3-CF3—C6H4 | NH | |
| 18 | CF3 | Br | 4-MeSO2—C6H4CO | 3,4-Cl2—C6H3 | O | |
| 19 | CF3 | Br | 2,4-F2—C6H3CS | 2,6-Cl2—C6H3 | O | |
| 20 | CN | I | 4-EtOCO—C6H4CO | 3-CF3—C6H4 | O | |
| 21 | CN | I | 3-Br-4-Cl—C6H3CO | 3-Cl—C6H4 | O | |
| 22 | CF3 | Br | i-Pr | 3-pyridinyl | S | |

TABLE 1-continued (1)

$$\text{Structure: thiazole with } R^1 \text{ at 4-position, } R^2 \text{ at 5-position, N at 2-position connected to } N=C(R^4)-X-R^3$$

| Compound No. | R1 | R2 | R3 | R4 | X | m.p. |
|---|---|---|---|---|---|---|
| 23 | CF3 | Cl | H | 1-naphthyl | NH | |
| 24 | CF3 | CN | 3,5-Me2—C6H3CO | 3-CF3—C6H4 | S | |
| 25 | CF3 | Br | 2-Br—C6H4CO | 3-CF3—C6H4 | O | |
| 26 | CF3 | I | Me2NCS | 3-CF3—C6H4 | S | 157–158 |
| 27 | CF3 | I | 4-Cl—C6H4CO | 2,6-F2—C6H3 | O | |
| 28 | CF3 | I | Et | 1-naphthyl | NH | |
| 29 | C2F5 | I | Ac | 3-Cl—C6H4 | O | |
| 30 | C2F5 | I | 1-imidazolyl | 3-CF3—C6H4 | | 143–144 |
| 31 | CF3 | CN | 1-imidazolyl | 3-CF3—C6H4 | | |
| 32 | CF3 | I | Me | 3-pyridinyl | NH | |
| 33 | CF3 | I | EtCO | 3-CF3—C6H4 | NH | |
| 34 | CF3 | Cl | Me | 4-t-Bu—C6H4 | S | |
| 35 | CF3 | I | H | 4-OMe—C6H4 | N—OEt | |
| 36 | CF3 | CN | H | 3-CF3—C6H4 | NH | |
| 37 | CN | Cl | i-Pr | 3-CF3—C6H4 | O | |
| 38 | CF3 | Br | Me | 2-CF3—C6H4 | S | |
| 39 | CF3 | Br | Me2NCS | 3-Cl—C6H4 | S | 147–148 |
| 40 | CF3 | Br | 2,4-F2—C6H3NH | 3-OCF3—C6H4 | NH | |
| 41 | CF3 | F | Et | 2,6-OMe2—C6H3 | S | |
| 42 | CF3 | CN | 4-SMe—C6H4CS | 4-Cl—C6H4 | O | |
| 43 | CF3 | Br | Pr-n | 2,4-F2—C6H3 | S | |
| 44 | CF3 | Br | 4-Cl—C6H4CO | C6H5 | S | |
| 45 | CF3 | I | H | 2,6-Cl2—C6H3 | N—O-allyl | |
| 46 | CF3 | Cl | Me | 3-OCF3—C6H4 | O | |
| 47 | CF3 | Cl | Et | C6H5 | S | |
| 48 | CF3 | Cl | Me | 4-Me—C6H4 | S | |
| 49 | CF3 | Cl | Me | 4-Cl—C6H4 | O | |
| 50 | CF3 | I | SO2Me | 2,4,6-Cl3—C6H2 | S | |
| 51 | CF3 | I | H | 4-C6H4—C6H4 | NH | |
| 52 | CF3 | I | Me2NCS | 4-n-C6H11—C6H4 | S | |
| 53 | CN | Br | Me | 3-Cl—C6H4 | S | |
| 54 | CF3 | I | 2-F-4-NO2—C6H3CO | 2,6-Cl2—C6H3 | O | |
| 55 | CF3 | CN | Me | 3-CF3—C6H4 | NMe | 107–109 |
| 56 | CF3 | Br | 4-F—C6H4CO | 4-C6H4O—C6H4 | S | |
| 57 | CF3 | Cl | MeNHCS | 2,4-Cl2—C6H3 | S | |
| 58 | CF3 | Cl | cyclopropyl | 2,6-Cl2—C6H3 | O | |
| 59 | CF3 | I | 4-CN—C6H4CO | 4-C6H4—C6H4 | S | |
| 60 | CF3 | Br | 4-Cl—C6H5CH2 | 2,4-Me2—C6H3 | S | |
| 61 | CF3 | Br | 2-EtOCO—C6H4CO | 4-C6H4O—C6H4 | O | |
| 62 | CF3 | Br | 4-SMe—C6H4CS | 4-Cl-2-Me—C6H3 | O | |
| 63 | CF3 | Br | Me | 2,4-F2—C6H3 | O | |
| 64 | CN | I | 2,4-Cl2—C6H3 | 3-CF3—C6H4 | S | |
| 65 | CF3 | Br | i-Pr | 2,6-(OMe)2—C6H3 | O | |
| 66 | CF3 | Cl | 2,4-Cl2—C6H3 | 4-Me—C6H4 | O | |
| 67 | C3F7 | I | 4-NO2—C6H4CO | 3-CF3—C6H4 | O | |
| 68 | CF3 | I | Me | 3,4-Cl2—C6H3 | S | |
| 69 | CF3 | Br | 2,4-F2—C6H3CS | 3-CN—C6H4 | O | |
| 70 | CF3 | I | 4-Br—C6H4CH2 | 3-CF3—C6H4 | S | oil |
| 71 | CF3 | I | 4-t-Bu—C6H4— | 4-CO2Et—C6H4 | O | |
| 72 | CF3 | Br | 2,4,6-Me3—C6H2CO | 3-F—C6H4 | O | |
| 73 | CF3 | Br | 1-imidazolyl | 2-Cl-4-CN—C6H3 | | |
| 74 | CF3 | Br | 3,5-Cl2—C6H3CO | 2-Cl-4-OMe—C6H3 | O | |
| 75 | CF3 | Cl | 4-F—C6H4 | 3-Cl—C6H4 | S | oil |
| 76 | CF3 | I | 4-Cl—C6H4CS | 1-naphthyl | S | |
| 77 | CF3 | I | Me | 3-Cl—C6H4 | N—O-allyl | |
| 78 | CF3 | I | n-C4H9 | 4-EtOCO—C6H4 | O | |
| 79 | CF3 | Cl | Me | 2,4-Cl2—C6H3 | O | |
| 80 | CN | Br | Et | 4-CF3—C6H4 | S | |
| 81 | CF3 | I | 3,5-Me2—C6H3CO | 3,4-Cl2—C6H3 | S | |
| 82 | CF3 | Cl | 4-OMe—C6H4CO | 2,4-F2—C6H3 | S | |
| 83 | CF3 | Br | Ac | 3-CF3—C6H4 | NH | |
| 84 | CF3 | Br | Ac | C6H5 | O | |

TABLE 1-continued (1)

| Compound No. | R1 | R2 | R3 | R4 | X | m.p. |
|---|---|---|---|---|---|---|
| 85 | CF3 | I | Ac | 3-CF3—C6H4 | N—OMe | 109–110 |
| 86 | CF3 | Br | allyl | 4-NO2—C6H4 | O | |
| 87 | CF3 | Br | t-BuNH | 3-CF3—C6H4 | NH | 113–114 |
| 88 | CF3 | Br | Et | 3-Ac—C6H4 | O | |
| 89 | CF3 | I | i-Pr | 3-CF3—C6H4 | NH | 83–84 |
| 90 | CF3 | Cl | C6H5NH | 4-Cl-3-NO2—C6H3 | NH | |
| 91 | CF3 | CN | cyclohexyl | 4-CF3—C6H4 | O | |
| 92 | CF3 | I | Et | 2-Cl-4-CF3—C6H3 | S | |
| 93 | CF3 | Br | H | 3-CF3—C6H4 | NH | |
| 94 | CF3 | I | Et | 3-CF3—C6H4 | O | |
| 95 | CF3 | I | H | 3-CF3—C6H4 | N—OMe | 107–108 |
| 96 | CF3 | I | 4-Cl—C6H4 | 3-OCF3—C6H4 | O | |
| 97 | CF3 | Cl | 3,5-Me2—C6H3CO | 3-Cl—C6H4 | O | 123–124 |
| 98 | CF3 | Cl | Me | 3-CF3—C6H4 | O | oil |
| 99 | CF3 | I | H | 3-CF3—C6H4 | NH | 107–108 |
| 100 | CF3 | Cl | N=C(4-Br—C6H4)Me | 3-Cl—C6H4 | O | |
| 101 | CF3 | I | 4-Cl—C6H4 | 2,4-Me2—C6H3 | S | |
| 102 | CF3 | I | 3,4-Br2—C6H3CO | 4-SMe—C6H4 | O | |
| 103 | CF3 | Cl | 4-t-Bu—C6H4 | 3-Cl—C6H4 | O | oil |
| 104 | CF3 | Cl | t-BuNH | 3,5-(CF3)2—C6H3 | NH | |
| 105 | CF3 | Cl | 4-CN—C6H4CO | 3,5-Me2—C6H3 | O | |
| 106 | CF3 | Cl | 4-OCF3—C6H4 | 3,4-Cl2—C6H3 | O | |
| 107 | CF3 | I | 2,6-F2—C6H3CO | 4-SO2Me—C6H4 | O | |
| 108 | CF3 | Br | Ac | 4-(Cl2C=CH)—C6H4 | S | |
| 109 | CF3 | Br | 3,4-Cl2—C6H4 | 4-AcOCH2—C6H4 | O | |
| 110 | CF3 | I | 4-CF3—C6H4 | C6H5CH2 | S | |
| 111 | CN | Br | Me | 4-CF3—C6H4 | S | |
| 112 | CF3 | I | 2,4-Cl2—C6H3 | 3,5-(CF3)2—C6H3 | O | |
| 113 | CF3 | I | Ac | 3-CF3—C6H4 | O | |
| 114 | CF3 | I | 4-OMe—C6H4CO | 3-CF3—C6H4 | O | |
| 115 | CF3 | I | 4-Cl—C6H4 | 3-CF3—C6H4 | SO2 | |
| 116 | CF3 | Cl | Me | 2,4-Cl2—C6H3 | S | |
| 117 | CF3 | I | 4-Me—C6H4 | 3-Cl—C6H4 | SO | |
| 118 | CF3 | Cl | 3-Cl—C6H4 | 2,4-F2—C6H3 | O | |
| 119 | CF3 | Cl | 4-NO2—C6H4CO | 4-t-Bu—C6H4 | O | |
| 120 | C2F5 | I | Me2NCS | 3-CF3—C6H4 | S | 149–150 |
| 121 | CF3 | Cl | Et | 3-CF3—C6H4 | S | oil |
| 122 | CN | Cl | 4-Cl—C6H4CO | 3-Cl—C6H4 | O | |
| 123 | CF3 | I | 2,4,6-Me3—C6H2CO | 3,5-(CF3)2—C6H3 | S | |
| 124 | CN | Br | 1-imidazolyl | 4-CF3—C6H4 | | |
| 125 | CF3 | I | 3,5-OMe2—C6H3CO | 2-CF3—C6H4 | S | |
| 126 | CF3 | F | i-Pr | 4-F—C6H4 | O | |
| 127 | CF3 | Cl | Me | 3-pyridinyl | O | |
| 128 | CN | I | 4-Me—C6H4 | 3,5-(CF3)2—C6H3 | O | |
| 129 | CN | Br | Me2NCS | 3-CF3—C6H4 | S | |
| 130 | CF3 | Cl | Me2NCS | 3-Cl—C6H4 | S | 130–131 |
| 131 | CF3 | Cl | Me2NCS | 2,4-F2—C6H3 | S | |
| 132 | CF3 | Cl | 3,5-Cl2—C6H3CO | 2,4,6-Me3—C6H2 | S | |
| 133 | CF3 | I | 4-Cl—C6H4CO | 3,5-(CF3)2—C6H3 | O | 121–122 |
| 134 | CF3 | Cl | Me | C6H5CH2 | S | |
| 135 | CF3 | CN | 3,5-Cl2—C6H3CO | 2,4-Cl2—C6H3 | O | |
| 136 | CF3 | CN | n-Pr | 3-CF3—C6H4 | S | |
| 137 | CF3 | Cl | 4-Me—C6H4CO | 3,4-Cl2—C6H3 | S | |
| 138 | CF3 | Br | 2,4-Br2—C6H3CO | 2,4-F2—C6H3 | O | |
| 139 | CF3 | Cl | 2,6-F2—C6H3CO | 3-CF3—C6H4 | O | |
| 140 | CF3 | I | 3-Cl—C6H4CO | 4-Cl—C6H4 | S | |
| 141 | CF3 | I | 4-Me2N—C6H4CO | 2,6-Cl2—C6H3 | O | |
| 142 | CF3 | CN | 4-t-Bu—C6H4 | 2,6-F2—C6H3 | O | |
| 143 | CF3 | I | 1-imidazolyl | 3-CF3—C6H4 | | 143–144 |
| 144 | CF3 | Br | 2-Cl-4-F—C6H3CO | 3,4-OCH2O—C6H3 | O | |
| 145 | CF3 | Br | 2,4-F2—C6H3CS | 4-Me2N—C6H4 | O | |
| 146 | CF3 | Cl | 4-F—C6H4 | 3-CF3—C6H4 | S | oil |
| 147 | C2F5 | H | H | 3-CF3—C6H4 | N—OMe | 179–180 |
| 148 | CF3 | Br | 3,5-Me2—C6H3CO | 3-CF3—C6H4 | NH | 155–156 |
| 149 | C2F5 | I | H | 3-CF3—C6H4 | N—OMe | 92–93 |
| 150 | C2F5 | H | 1-imidazolyl | 3-CF3—C6H4 | | |

TABLE 2

NMR spectral data of oily substances

| Compound No. | 1H-NMR (ppm) |
| --- | --- |
| 70 | 4.35 (broad s, 2H), 7.1–7.3 (m, 2H), 7.4–7.7 (m, 4H), 7.7–7.8 (m, 2H) |
| 75 | 6.92 (t, 2H), 7.2–7.5 (m, 5H), 7.62 (s, 1H) |
| 98 | 4.10 (s, 3H), 7.53 (t, 1H), 7.66 (d, 1H), 7.75 (d, 1H), 7.83 (s, 1H) |
| 103 | 1.30 (s, 9H), 6.7–7.0 (m, 2H), 7.2–8.1 (m, 6H) |
| 121 | 1.34 (t, 3H), 3.15 (q, 2H), 7.5–7.7 (m, 2H), 7.78 (d, 2H) |
| 146 | 6.8–7.0 (m, 2H), 7.2–7.3 (m, 2H), 7.45 (t, 1H), 7.62 (d, 1H), |

What is claimed is:

1. An insecticide or acaricide wherein the insecticide or acaricide includes a compound having at least one of a thiazole derivative of formula (1):

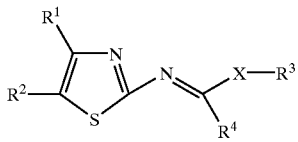

(1)

wherein $R^1$ is CN or fluoroalkyl (especially $C_1$–$C_4$ fluoroalkyl), $R^2$ is H, halogen or CN, $R^3$ is aryl, phenylalkyl, alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), X is O, $SO_n$, n is 0, 1 or 2, or X is $N(R^5)$ wherein, $R^3$ and $R^5$ are, independently, H or alkyl, alkoxy, acyl, alkylamino, aryl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or $R^3$ and $R^5$ may additionally be fused to a heteroaromatic ring.

2. An agrochemical composition comprising an insecticidally or acaricidally effective amount of a compound having at least one of a thiazole derivative of formula (1)

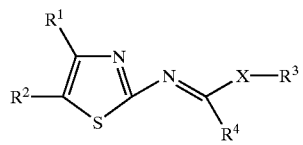

(1)

wherein $R^1$ is CN or fluoroalkyl (especially $C_1$–$C_4$ fluoroalkyl), $R^2$ is H, halogen or CN, $R^3$ is aryl, phenylalkyl, alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), X is O, $SO_n$, n is 0, 1 or 2, or X is $N(R^5)$ wherein, $R^3$ and $R^5$ are, independently, H or alkyl, alkoxy, acyl, alkylamino, aryl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or $R^3$ and $R^5$ may additionally be fused to a heteroaromatic ring.

3. A thiazole derivative of formula (1):

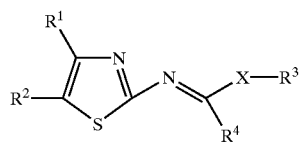

(1)

wherein $R^1$ is CN or fluoroalkyl (especially $C_1$–$C_4$ fluoroalkyl), $R^2$ is H, halogen or CN, $R^3$ is aryl, phenylalkyl, alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), X is O, $SO_n$, n is 0, 1 or 2, or X is $N(R^5)$ wherein, $R^3$ and $R^5$ are, independently, H or alkyl, alkoxy, acyl, alkylamino, aryl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkoxy or alkoxycarbonylalkoxy), or $R^3$ and $R^5$ may additionally be fused to a heteroaromatic ring.

4. An insecticidal or acaricidal composition comprising a thiazole derivative of formula (1):

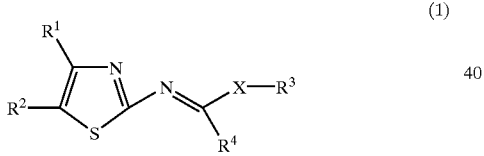
(1)

wherein $R^1$ is CN or fluoroalkyl (especially $C_1$–$C_4$ fluoroalkyl), $R^2$ is H, halogen or CN, $R^3$ is aryl, phenylalkyl, alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), X is O, $SO_n$, n is 0, 1 or 2, or X is $N(R^5)$ wherein, $R^3$ and $R^5$ are, independently, H or alkyl, alkoxy, acyl, alkylamino, aryl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or $R^3$ and $R^5$ may additionally be fused to a heteroaromatic ring.

5. A process for preparing a compound of formula (1)

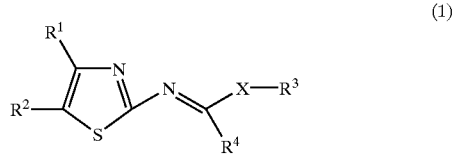
(1)

comprising the steps of:

reacting a compound of the general formula (2)

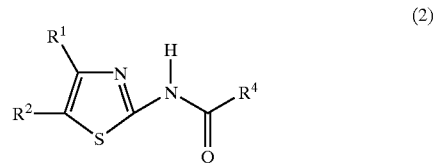
(2)

in which $R^1$ is CN or fluoroalkyl (especially $C_1$–$C_4$ fluoroalkyl), $R^2$ is H, halogen or CN, $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy) with phosphorous pentachloride and phosphorous oxychloride to produce the intermediate (3);

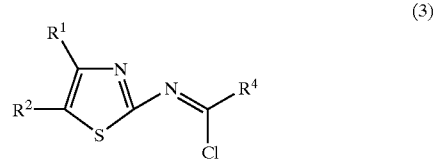
(3)

reacting a compound of the general formula (3) in which $R^1$ is CN or fluoroalkyl (especially $C_1$–$C_4$ fluoroalkyl), $R^2$ is H, halogen or CN, $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy) with $R^3$—X—A in which X is O or S, $R^3$ is alkyl, alkenylalkyl, alkynylalkyl, acyl, benzyl, aryl, aroyl or alkylthiocarbonyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or alkylthiocarbamoyl and A is an alkali metal radical such as Na or K, or $R^3$—X—H in which X is N—$R^5$, $R^5$ is H, alkyl, alkoxy, acyl, alkylamino, aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or arylamino (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), or $R^3$ and $R^5$ may additionally be fused to a heteroaromatic ring with an inorganic base such as NaH, NaOH, KOH, $K_2CO_3$, $Na_2CO_3$ or an organic amine such as pyridine, triethylamine, imidazole to produce (1) and reacting a compound of the general formula (3) in which $R^1$ is CN or fluoroalkyl (especially $C_1$–$C_4$ fluoroalkyl), $R^2$ is H, halogen or CN, $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy) with thiourea to produce the intermediate (4) followed by reacting an alkali metal salt of the general formula (4) with $R^3$—Y in which $R^3$ is alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl

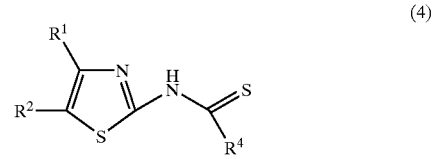

(being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), and Y is halogen to produce (1) in which $R^1$ is CN or fluoroalkyl (especially $C_1$–$C_4$ fluoroalkyl), $R^2$ is H, halogen or CN and $R^4$, $R^4$ is aryl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy) and X is S and $R^3$ is phenylalkyl, alkyl, cycloalkyl groups (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy), alkylthiocarbamoyl, or aroyl (being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy).

\* \* \* \* \*